(12) United States Patent
Song et al.

(10) Patent No.: US 12,597,485 B2
(45) Date of Patent: Apr. 7, 2026

(54) ASSESSMENT METHOD AND DEVICE FOR INFECTIOUS DISEASE TRANSMISSION, COMPUTER EQUIPMENT AND STORAGE MEDIUM

(71) Applicant: SOUTHERN UNIVERSITY OF SCIENCE AND TECHNOLOGY, Shenzhen City (CN)

(72) Inventors: Xuan Song, Shenzhen City (CN); Zipei Fan, Shenzhen City (CN); Renhe Jiang, Shenzhen City (CN); Chuang Yang, Shenzhen City (CN); Zhiwen Zhang, Shenzhen City (CN); Quanjun Chen, Shenzhen City (CN); Ryosuke Shibasaki, Shenzhen City (CN)

(73) Assignee: SOUTHERN UNIVERSITY OF SCIENCE AND TECHNOLOGY, Guangdong (CN)

( * ) Notice: Subject to any disclaimer, the term of this patent is extended or adjusted under 35 U.S.C. 154(b) by 1226 days.

(21) Appl. No.: 17/488,792

(22) Filed: Sep. 29, 2021

(65) Prior Publication Data

US 2023/0098491 A1     Mar. 30, 2023

(51) Int. Cl.
| | |
|---|---|
| *G16B 20/00* | (2019.01) |
| *G16B 50/00* | (2019.01) |
| *G16H 50/00* | (2018.01) |

(52) U.S. Cl.
CPC ............. *G16B 20/00* (2019.02); *G16B 50/00* (2019.02); *G16H 50/00* (2018.01)

(58) Field of Classification Search
None
See application file for complete search history.

(56) References Cited

U.S. PATENT DOCUMENTS

| | | | | |
|---|---|---|---|---|
| 11,003,880 B1* | 5/2021 | Smart | .................... | G06Q 50/01 |
| 12,266,451 B2* | 4/2025 | Yoo | ......................... | H04W 4/90 |
| 2022/0030382 A1* | 1/2022 | Klasson | ................ | G16H 40/20 |
| 2022/0384056 A1* | 12/2022 | Gopalakrishnan | ..... | G16H 50/80 |

FOREIGN PATENT DOCUMENTS

| | | |
|---|---|---|
| CN | 111739653 A | 10/2020 |

OTHER PUBLICATIONS

Benreguia et al. (IEEE Access (2020) vol. 8; 145242-145255).*
Dansana et al. (Computers, Materials & Continua (2021) vol. 67, No. 2:1595-1612).*
Heng et al. (Scientific Reports (2020) vol. 10:6 pages).*
Wang et al. (Machine Learning: Science and Technology (2021) vol. 2:12 pages).*
Yang et al. (Journal of Thoracic Disease (2020) vol. 12(3):165-174).*

* cited by examiner

*Primary Examiner* — Lori A. Clow
(74) *Attorney, Agent, or Firm* — OLIFF PLC

(57) ABSTRACT

The invention provide an assessment method and device for infectious disease transmission, computer equipment and storage medium. The method comprises: obtaining respective target track data corresponding to assessment objects within a preset area in a first time slice; determining a matching subarea to which each assessment object matches in the first time slice based on the target track data; taking at least one of the plurality of subareas as a target subarea, and assessing an assessment object within the target subarea based on an infectious disease model to determine a transmission trend of an infectious disease for the assessment object within the preset area in the first time slice; and taking a next time slice as the first time slice, and re-performing the above steps until end of the target time period to determine a transmission trend of the infectious disease among the assessment objects during the target time period.

20 Claims, 4 Drawing Sheets

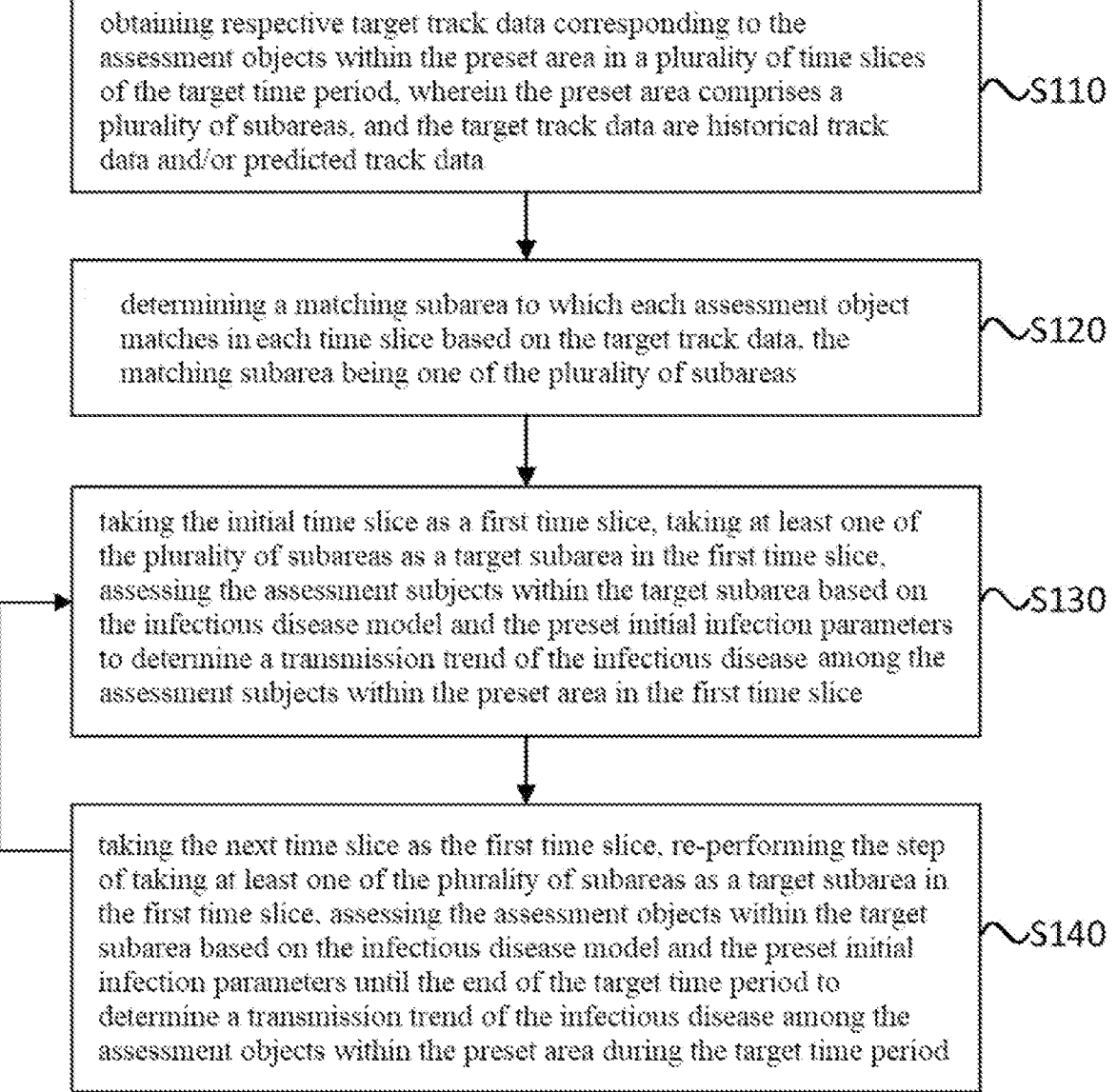

obtaining respective target track data corresponding to the assessment objects within the preset area in a plurality of time slices of the target time period, wherein the preset area comprises a plurality of subareas, and the target track data are historical track data and/or predicted track data — S110 determining a matching subarea to which each assessment object matches in each time slice based on the target track data, the matching subarea being one of the plurality of subareas — S120 taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice — S130 taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period — S140

Fig. 1

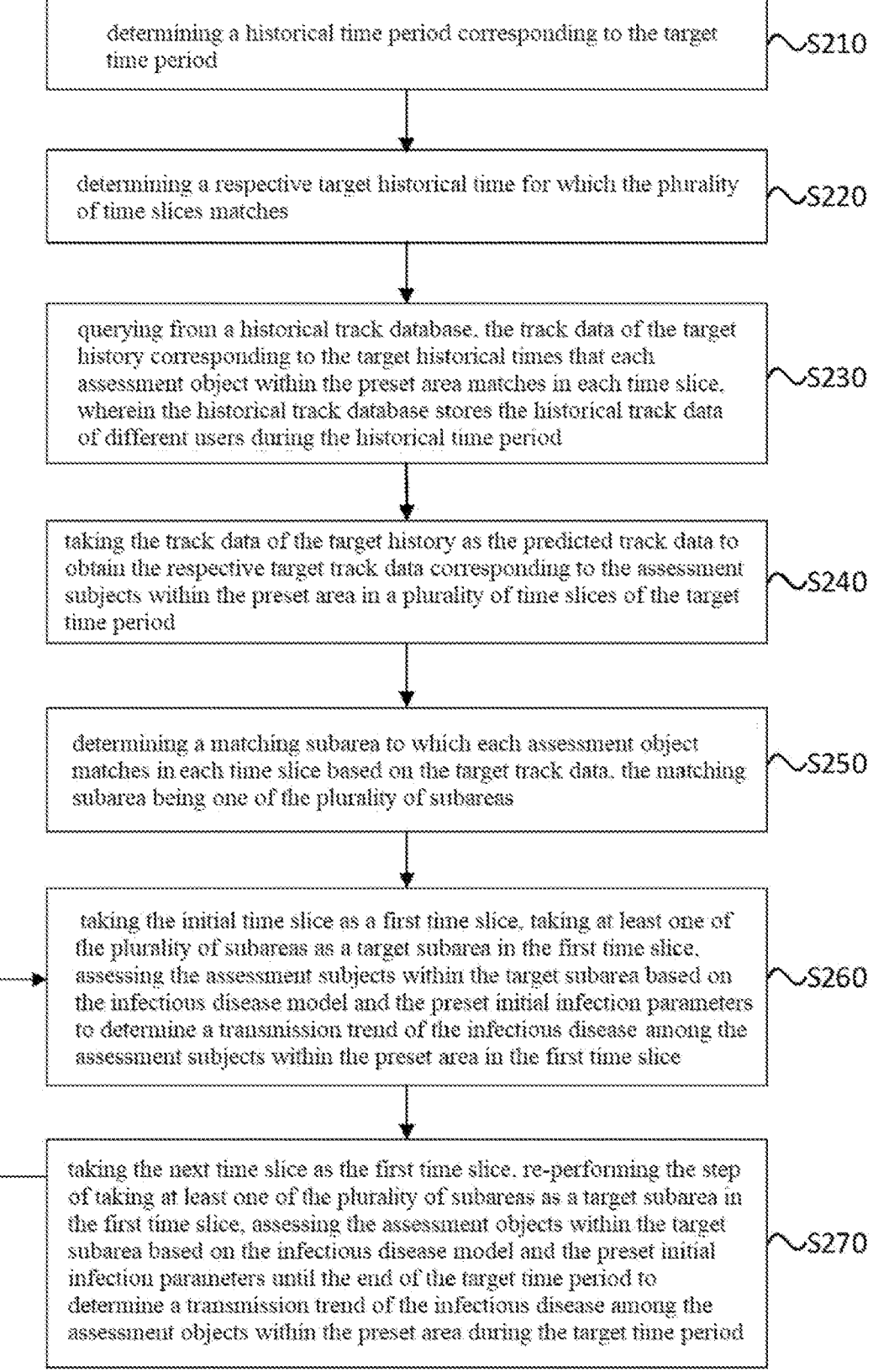

determining a historical time period corresponding to the target time period                                    ∿S210 determining a respective target historical time for which the plurality of time slices matches                                    ∿S220 querying from a historical track database, the track data of the target history corresponding to the target historical times that each assessment object within the preset area matches in each time slice, wherein the historical track database stores the historical track data of different users during the historical time period                                    ∿S230 taking the track data of the target history as the predicted track data to obtain the respective target track data corresponding to the assessment subjects within the preset area in a plurality of time slices of the target time period                                    ∿S240 determining a matching subarea to which each assessment object matches in each time slice based on the target track data, the matching subarea being one of the plurality of subareas                                    ∿S250 taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice                                    ∿S260 taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period                                    ∿S270

Fig. 2

ASSESSMENT METHOD AND DEVICE FOR INFECTIOUS DISEASE TRANSMISSION, COMPUTER EQUIPMENT AND STORAGE MEDIUM

TECHNICAL FIELD

Embodiments of the present invention relate to the technical field of intelligent prediction, in particular to an assessment method and device for infectious disease transmission, computer equipment and storage medium.

BACKGROUND

The track simulation assessment has an important significance and role in disease prevention and control, etc.

At present, the common way to assess the transmission is to analyze the development process of areal diseases and assess the variation trend based on simulation models of infectious diseases, which is mostly through mathematical models (classified into ordinary differential equations, partial differential equations and network dynamics models) for the population size within an area.

However, these models focus on the simulation and estimation of the overall number of patients, do not consider the real transmission process of infection, cannot assess the infection trend in each area at a fine-grained level, and the information obtained by the assessment is limited.

SUMMARY OF THE INVENTION

Embodiments of the present invention provide an assessment method and device for infectious disease transmission, computer equipment and storage medium to achieve the technical effect of fine-grained assessment of the trend of infection of respective areas.

In a first aspect, an embodiment of the present invention provides an assessment method for infectious disease transmission, comprising:

obtaining respective target track data corresponding to the assessment objects within the preset area in a plurality of time slices of the target time period, wherein the preset area comprises a plurality of subareas, and the target track data are historical track data and/or predicted track data;

determining a matching subarea to which each assessment object matches in each time slice based on the target track data, the matching subarea being one of the plurality of subareas;

taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; and taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

Optionally, prior to the obtaining respective target track data corresponding to the assessment objects within the preset area in a plurality of time slices of the target time period, the method comprises:

obtaining the respective non-segmented raw track data corresponding to the assessment objects within the preset area during the target time period; and segmenting the respective non-segmented raw track data corresponding to the assessment objects within the preset area according to a plurality of time slices of the target time period to obtain the respective target track data corresponding to the assessment objects within the preset area in the plurality of time slices of the target time period.

Optionally, the infectious disease model is a SEIR model, and the assessing the assessment subjects within the target subarea based on the infectious disease model and the preset initial infection parameters, comprising: determining the infected subjects, carriers, recovered persons and uninfected subjects within the target subarea in the first time slice; and simulating the infectious disease transmission among the infected subjects, carriers, recovered persons and uninfected subjects within the target subarea based on a SEIR model to obtain the transmission trend of the infectious disease within the target subarea in the first time slice.

Optionally, the obtaining respective target track data corresponding to the assessment objects within the preset area in a plurality of time slices of the target time period comprises:

receiving an initial assessment instruction generated by the user upon selecting at least the initial infection parameters, the preset area, and the target time period;

obtaining respective target track data corresponding to the assessment objects within the preset area in a plurality of time slices of the target time period and the initial health status of the initial time slice based on the initial assessment instruction;

wherein the assessing the assessment subjects within the target subarea based on the infectious disease model and the preset initial infection parameters comprises:

assessing the transmission of the disease among the assessment objects within the target subarea in the first time slice based on the infectious disease model and the respective initial health status corresponding to the assessment objects within the target subarea.

Optionally, the target track data is predicted track data, and the obtaining the respective target track data corresponding to the assessment objects within the preset area in a plurality of time slices of the target time period comprises:

determining a historical time period corresponding to the target time period;

determining a respective target historical time for which the plurality of time slices matches;

querying from a historical track database, the track data of the target history corresponding to the target historical times that each assessment object within the preset area matches in each time slice, wherein the historical track database stores the historical track data of different users during the historical time period; and taking the track data of the target history as the predicted track data to obtain the respective target track data corresponding to the assessment subjects within the preset area in a plurality of time slices of the target time period.

Optionally, the target track data is predicted track data, and the obtaining the respective target track data corresponding to the assessment objects within the preset area in a plurality of time slices of the target time period comprises:

invoking a prepared control plan, the control plan being used to influence the travel of the assessment subjects and/or to influence the infectious disease transmission, and determining, based on the control plan, the respective target track data corresponding to the assessment objects within the preset area in a plurality of time slices of the target time period.

Optionally, the control plan comprises at least one of area lockdown, teleworking, and setting detection points, the method further comprising:

if the control plan comprises area lockdown, the predicted track data corresponding to a predicted subject affected by the area lockdown with another unaffected historical track data before the transmission simulation;

if the control plan comprises teleworking, the predicted track data corresponding to a predicted subject affected by the teleworking at the affected time is replaced with the corresponding home location before the transmission simulation; and if the control plan comprises setting detection points, the detection probability is set at a corresponding target subarea, and the target track data corresponding to the predicted subject for which an abnormality is detected is replaced to a safe subarea among the plurality of subareas during the transmission simulation from the current time slice until the end of the target time period.

In a second aspect, an embodiment of the present invention provides an assessment device for infectious disease transmission, comprising:

a track data acquisition module for obtaining respective target track data corresponding to the assessment objects within the preset area in a plurality of time slices of the target time period, the preset area comprising a plurality of subareas, wherein the target track data is historical and/or predicted track data;

an area matching module for determining a matching subarea to which each assessment object matches in each time slice based on the target track data, the matching subarea being one of the plurality of subareas;

an assessment module for taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; and a moment switch module for taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

In a third aspect, an embodiment of the present invention provides a computer equipment, comprising:

one or more processors;

storage device for storing one or more computer programs;

the one or more computer programs, when executed by the one or more processors, enable the one or more processors to implement the assessment method for infectious disease transmission as described in any embodiment of the present invention.

In a fourth aspect, an embodiment of the present invention provides a computer-readable storage medium, on which a computer program is stored, wherein the computer program, when executed by a processor, implements the assessment method for infectious disease transmission as described in any embodiment of the present invention.

Embodiments of the present invention obtain respective target track data corresponding to the assessment objects within the preset area in a plurality of time slices of the target time period, the preset area comprising a plurality of subareas, wherein the target track data is historical and/or predicted track data; determining a matching subarea to which each assessment object matches in each time slice based on the target track data, the matching subarea being one of the plurality of subareas; taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period; solves the problem that the models focus on the simulation and estimation of the overall number of patients and do not consider the real transmission process of infection, resulting in less accurate assessment results, and achieves the technical effect of fine-grained assessment of the trend of infection of respective areas.

DESCRIPTION OF THE DRAWINGS

FIG. 1 is a schematic flowchart illustrating an assessment method for infectious disease transmission provided in Embodiment I of the present invention;

FIG. 2 is a schematic flowchart illustrating an assessment method for infectious disease transmission provided in Embodiment II of the present invention;

DETAILED DESCRIPTION

Figure 3:
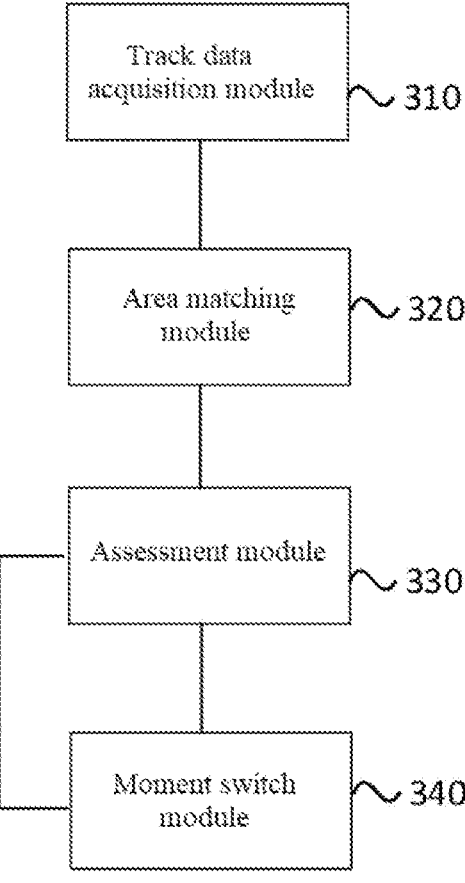
FIG. 3 is a schematic structural diagram of an assessment device for infectious disease transmission provided in Embodiment III of the present invention.

The present invention will be described in further detail with reference to the drawings and embodiments. It is to be understood that the specific embodiments described herein are merely illustrative of the present invention and are not to be construed as limiting the invention. It should be further noted that, for the convenience of description, only some structures related to the present invention are shown in the drawings, not all of them.

Before discussing exemplary embodiments in greater detail, it should be noted that some exemplary embodiments are described as processes or methods depicted as flow-charts. Although the flowcharts may describe the steps as a sequential process, many of the steps can be performed in parallel, concurrently, or simultaneously. In addition, the order of the steps may be rearranged. The process may be terminated when its operations are completed, but could have additional steps not comprised in the drawings. The processes may correspond to methods, functions, procedures, subroutines, subprograms, etc.

In addition, the terms "first", "second", and the like, may be used herein to describe various directions, actions, steps, or elements, etc., but these directions, actions, steps, or elements are not limited by these terms. These terms are only used to distinguish a first direction, action, step, or element from another direction, action, step, or element. By way of example, without departing from the scope of the present application, a first information may be referred to as a second information, and similarly, a second information may be referred to as a first information. Both the first information and the second information are information, but they are not the same information. The terms "first", "second", and the like, are not to be construed to indicate or imply relative importance or to implicitly indicate the number of technical features indicated. Thus, a feature that is defined as "first", "second" may comprise one or more such features, either explicitly or implicitly. In the description of the present invention, "a plurality of" means at least two, e.g., two, three, etc., unless specifically defined otherwise.

Embodiment I

FIG. 1 is a schematic flow chart of an assessment method for the infectious disease transmission provided in Embodiment I of the present invention, applicable to a scenario for assessing the transmission trend of infectious disease, and the method may be performed by an assessment device for infectious disease transmission, which device may be implemented in software and/or hardware and may be integrated in a computer equipment.

As shown in FIG. 1, the assessment method for infectious disease transmissions by Embodiment I of the present invention comprises:

S110, obtaining respective target track data corresponding to the assessment objects within the preset area in a plurality of time slices of the target time period, wherein the preset area comprises a plurality of subareas, and the target track data are historical track data and/or predicted track data;

Wherein, the track data refers to the data information obtained by sampling the motion process of one or more moving objects in a spatiotemporal environment, comprising device number, location of sampling points, sampling time, velocity, etc., these sampling point data information constitutes track data according to device number and sampling order. The target time period is a time period that needs to be assessed. Specifically, the target time period comprises a time slice for characterizing a time period. The target track data is track data corresponding to each assessment object. It should be noted that the target track data is historical track data and/or predicted track data. Specifically, when the target track data is historical track data, the method of this embodiment can be used to identify the close contacts of an infected person or a latent person after an infected person or latent person is known, so that the close contacts can be isolated and observed, tested, etc., to reduce the risk of transmission; and when the target track data is predicted track data, the method of this embodiment can be used to predict the transmission trend of an infectious disease in the future. The first time slice is a time period of a predetermined length of time, and can be, for example, 5 minutes, 10 minutes, etc. when the target track data is historical track data, the first time slice is one of the time periods of the historical moment; and when the target track data is predicted track data, the first time slice is one of the time periods of the future. It can be understood that this embodiment provides examples of application only and is not limited to a specific application. In this embodiment, the preset area is used to characterize a geographical location, and the preset area can be selected as desired, for example, the entire country or a geographical area, etc., without limitation herein. For example, when the preset area is Wuhan, the plurality of subareas may be divided according to administrative regions, or can be divided according to each fixed area, for example, one subarea for every 50 square meters, without any specific limitation herein.

In an optional embodiment, prior to said obtaining respective target track data corresponding to the assessment objects within the preset area in a plurality of time slices of the target time period, the method comprises:

obtaining the respective non-segmented raw track data corresponding to the assessment objects within the preset area during the target time period; segmenting the respective non-segmented raw track data corresponding to the assessment objects within the preset area according to a plurality of time slices of the target time period to obtain the respective target track data corresponding to the assessment objects within the preset area in the plurality of time slices of the target time period.

Wherein, the unsegmented raw track data may be track data of one day or one hour, which may be obtained by positioning an assessment object using a mobile terminal. When obtaining the target track data of the first time slice, the target track data corresponding to the first time slice may be obtained through the unique identification of the assessment object.

S120, determining a matching subarea to which each assessment object matches in each time slice based on the target track data, the matching subarea being one of the plurality of subareas;

wherein the matching subarea is a subarea in which the target track data of the assessment object is located in a plurality of subareas in the first time slice. For example, in the first time slice, the target track data of the assessment object A is located in Wuhan Optics Valley, then the matching subarea of the assessment object A is the Optics Valley. Specifically, the matching subarea is related to the way of dividing a plurality of subareas in a preset area. It should be noted that the first time slice is a time period, then the track point corresponding to the beginning moment of the first time slice can be determined as the matched matching subarea, or the track point corresponding to the beginning moment of the first time slice can be determined as the matched matching subarea, or the various estimated points of the first time slice can be merged to determine the matched matching subarea.

S130, taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice;

Wherein, the target subarea refers to at least one of the plurality of subareas. Specifically, after determining the matching subareas to which each assessment object matches, each subarea comprises a corresponding assessment object, the assessment object of the target subarea may be assessed to determine a transmission trend of the infectious disease for the assessment object within the preset area in the first time slice. It should be noted that in the present embodiment, the target subarea is assessed individually by the infectious disease model to determine the transmission trend within the preset area. It should be understood that in the present embodiment, the assessment of the transmission trend by the user's track data in combination with the infectious disease model takes into account the contact relationship between the predicted objects, not only the total number of persons infected, but the technical solution of the present embodiment assesses a finer granularity to better reflect the real transmission trend, as compared to the conventional mathematical model for prediction. It should be understood that in the further embodiment, the target subarea is assessed individually through the infectious disease model, and it is not necessary to takes into account the contact relationship between the assessment objects within the entire preset area, but only the contact relationship between the assessment objects within each target subarea, which greatly reduces the computational effort and reduces the computing power requirement for computer equipment, as compared to the assessment of the contact relationship of each user for the entire preset area. Optionally, the target subarea may be selected as an area in which the number of persons comprised in the plurality of subareas is greater than or equal to the predetermined number of persons. For example, when the predetermined value is two, only regions with more than two people in the plurality of subareas are simulated, further reducing the computational effort.

In an optional embodiment, the infectious disease model is a SEIR model, and the assessing the assessment subjects within the target subarea based on the infectious disease model and the preset initial infection parameters, comprising:

determining the infected subjects, carriers, recovered persons and uninfected subjects within the target subarea in the first time slice; simulating the infectious disease transmission among the infected subjects, carriers, recovered persons and uninfected subjects within the target subarea based on a SEIR model to obtain the transmission trend of the infectious disease within the target subarea in the first time slice.

Wherein, the infected subject means a subject considered to be infected with the infectious disease and symptomatic, the carrier means a subject carrying infectious microorganisms such as virus or bacteria but not symptomatic during the latent period, the uninfected subject means a subject considered to be not infected with the infectious disease, and the recovered person means a subject gaining immunity through self-healing or therapy. Specifically, the infected subject, the carrier, and the recovered person within the target subarea are determined by initial infection parameters comprising: initial infected subject, carrier, and recovered person distribution information in each subarea, basic infection parameters of the infectious disease such as the infectiousness size, etc., upon performing the initial assessment. The initial infection parameters may be determined using historical medical data or may be empirically determined by an expert, without limitation herein, when the method of the present embodiment is continuously being assessed, the infected subject, the carrier, the recovered person, and the uninfected subject in the current time slice are determined based on the result of the assessment in the previous time slice.

The SEIR model is an infectious disease transmission model and is one of the most classic models of infectious diseases. For a specific target subarea, the population information for the subarea (number of infected subjects, carrier, recovered persons, and non-infected subjects) in the current time slice is input into the SEIR transmission model for calculation, resulting in the transmission trend of the infectious disease in non-infected subjects. Optionally, the SIR model can also be selected to be simulated as needed, without limitation herein. Carriers are not considered in the SIR model, and a suitable model can be selected for prediction based on the specific characteristics of the infectious disease, without limitation herein.

It will be appreciated that the simulation may be performed with other infectious disease models and corresponding parameters, which is not specifically limited by this embodiment.

S140, taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

Wherein the next time slice is the next time slice adjacent to the first time slice, with no gap between the two. For example, when the first time slice is 9:00-9:05, the next time slice is 9:05-9:10. The preset time length may be set as desired, and is not particularly limited herein. Specifically, the present embodiment starts from the initial time slice of the target time period and re-performs step S110 every other time slice, and stops the assessment when the next time slice exceeds the target time period, thereby determining the transmission trend of the infectious disease among the assessment objects within the preset area during the target time period.

Optionally, step S110, obtaining respective target track data corresponding to the assessment objects within the preset area in the first time slice, and in particular, receiving an initial assessment instruction generated by the user upon selecting at least the initial infection parameters, the preset area, and the target time period; obtaining respective target track data corresponding to the assessment objects within the preset area in a plurality of time slices of the target time period and the initial health status of the initial time slice based on the initial assessment instruction. Transmission of the disease among the assessment objects within the target subarea in the first time slice may be assessed based on the infectious disease model and the respective initial health status corresponding to the assessment objects within the target subarea.

Specifically, the user of the computer equipment may generate an initial assessment instruction instructing the computer equipment to start assessment upon selecting the initial infection parameters, the preset area to be assessed, and the target time period on the display panel of the computer equipment as needed, and the computer equipment, upon receiving the initial assessment instruction, starts obtaining the respective target track data corresponding to the assessment objects within the preset area in the first time slice, and performs assessment according to the initial infection parameters.

The technical solution according to an embodiment of the present invention obtains respective target track data corresponding to the assessment objects within the preset area in a plurality of time slices of the target time period, the preset area comprising a plurality of subareas, wherein the target track data is historical and/or predicted track data; determining a matching subarea to which each assessment object matches in each time slice based on the target track data, the matching subarea being one of the plurality of subareas; taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period; assessing the transmission trend by using the track data of the assessment objects, considering the contact process among different assessment objects, the technical effect of fine-grained assessment of the trend of infection of respective areas is achieved compared to analyzing the progress of regional disease and assessing the change trend for the population size within the area by a mathematical model (which may be classified as ordinary differential equation, partial differential equation, and network dynamics model).

Embodiment II

FIG. 2 is a schematic flowchart of an assessment method for the infectious disease transmission provided in Embodiment II of the present invention. This embodiment is a further refinement of the above-mentioned technical solution, wherein the target track data of this embodiment is predicted track data applicable to a scenario for assessing the future transmission trend of infectious disease. The method may be performed by an assessment device for infectious disease transmission, which device may be implemented in software and/or hardware and may be integrated in a computer equipment.

As shown in FIG. 2, the assessment method for the infectious disease transmission provided in Embodiment II of the present invention comprises:

S210, determining a historical time period corresponding to the target time period.

S220, determining a respective target historical time for which the plurality of time slices matches;

wherein the target historical time that the time slice matches is a historical time in the past to which the time slice is mapped. For example, the time slice is 9:00-9:05 a.m. on Jul. 1, 2020, then 9:00-9:05 a.m. on Jul. 1, 2019 is used as the target historical time matched by the at time slice.

S230, querying from a historical track database, the track data of the target history corresponding to the target historical times that each assessment object within the preset area matches in each time slice, wherein the historical track database stores the historical track data of different users during the historical time period;

Wherein, the historical track database refers to a database with pre-stored historical track data of different users in historical time period. The historical track data refers to the track data of the past time, which actually exists. Wherein, the historical time period can be set as needed, for example, it can be from the 1st to the 31st as a historical time period, and for example, it can be from Monday to Sunday as a historical time period, and it can also be a year as a historical time period. Specifically, after determining the target historical time corresponding to the first time slice, the track data of the target history corresponding to the assessment object in the target historical time can be queried from the historical track database by the unique identification of each assessment object.

Optionally, when the unique identifier corresponding to the predicted object does not exist in the historical track database, the information of the target predicted object for which the corresponding unique identifier does not exist in the historical track database may be compared with the information of other predicted objects, and the one with the highest similarity obtained by the comparison is used as the matching object of the target predicted object, the track data of the target history corresponding to the matching object at the target historical time is used as the track data of the target history corresponding to the target predicted object at the target historical time. When the unique identifier corresponding to the target predicted object exists in the track database of the history, but the track data of the target history corresponding to the target historical time does not exist, the track data of the history corresponding to the previous historical time of the target predicted object in the target historical time can be used as the track data of the target history corresponding to the target historical time. Specifically, at least one of a date type (such as a workday or a rest day) and a month corresponding to the target historical time may be determined, and a matching previous historical time may be selected. For example, if the target historical time corresponds to a Monday, last Monday is selected as the previous historical time.

S240, taking the track data of the target history as the predicted track data to obtain the respective target track data corresponding to the assessment subjects within the preset area in a plurality of time slices of the target time period.

In this step, the track data of the target history is used as the predicted track data, so as to obtain the respective predicted track data corresponding to the assessment subjects within the preset area in the first time slice.

S250, determining a matching subarea to which each assessment object matches in each time slice based on the target track data, the matching subarea being one of the plurality of subareas, the target track data being predicted track data;

S260, taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice;

S270, taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

In an optional embodiment, obtaining the respective target track data corresponding to the assessment objects within the preset area in a plurality of time slices of the target time period, which comprises:

invoking a prepared control plan, the control plan being used to influence the travel of the assessment subjects and/or to influence the infectious disease transmission, and determining, based on the control plan, the respective target track data corresponding to the assessment objects within the preset area in a plurality of time slices of the target time period.

In this embodiment, the target track data corresponding to each assessment object is determined by the control plan, and then the determination of the matching subareas is performed, so that the assessment of the transmission trend can be performed. Wherein, this can be expressed by the following formula:

$\Gamma'=\theta_{mob}(\Gamma\Phi)$, where $\Phi$ denotes the simulated implemented prevention and control policy, F is the population movement pattern before the implementation of the control plan, $\Gamma$ denotes the characteristics of the population activity pattern restricted by the control plan, and $\theta_{mob}$ denotes the generation model for the predicted track data under the influence of the control plan.

Specifically, if the control plan comprises area lockdown, the predicted track data corresponding to a predicted subject affected by the area lockdown is replaced with another unaffected historical track data before the transmission simulation; if the control plan comprises teleworking, the predicted track data corresponding to a predicted subject affected by the teleworking at the affected time is replaced with the corresponding home location before the transmission simulation; and if the control plan comprises setting detection points, the detection probability is set at a corresponding target subarea, and the target track data corresponding to the predicted subject for which an abnormality is detected is replaced to a safe subarea among the plurality of subareas during the transmission simulation from the current time slice until the end of the target time period.

Wherein the predicted object affected by the area lockdown is a predicted object whose target track data intersects with the lockdown area. Another track data is a track not affected by the area lockdown policy, and maps a historical track not affected by the area lockdown policy. For example, where the lockdown area is Nanshan District through which the target track data of a predicted object A passes, then the track data of the predicted object A is replaced with the track data that does not pass through the Nanshan District based on the historical track database.

The predicted object affected by the teleworking refers to users who need to go to work in a lockdown workplace during the affected period. If the first time slice belongs to a workday, the target track data corresponding to the predicted object affected by the teleworking is replaced with a corresponding home location. Specifically, the track points of the historical track data of the predicted object can be analyzed to define the location where the predicted object is located during the working hours of the workdays as the workplace, and the location where the predicted object is located during the non-working hours of the rest days or the workdays as the home location. Specifically, the candidate workplace and the candidate home location can be automatically determined based on the track points of the historical track data and a time threshold and a spatial threshold value for stopping point detection (e.g., the stopping time exceeds 1 hour and the distance of the cluster of stopping track points is less than 500 meters), and the location with the most number of stops during the non-working hours (e.g., 0-6 o'clock) is defined as the home location, and the location with the most number of stops during the working hours (e.g., 11-17 o'clock) is defined as the workplace.

The purpose of setting detection points is to set sites that detect the health status of the user, specifically, sites that detect whether the user has developed symptoms of illness, such as sites that detect the user's body temperature. The detection probability $\beta$ is the probability that an infected person and a carrier can be detected. The detection probability can be determined based on the probability of historical detection, or it can be a probability value given empirically by an infectious specialist. Specifically, infected persons and carriers within the target subarea have a $\beta$ probability of being detected within a given time slice, i.e., abnormal predicted objects can be detected in this embodiment. The safety subarea may be the location mapping the hospital. Specifically, the target track data corresponding to the detected abnormal predicted object is replaced to the safe subarea for a prediction of transmission trends.

This embodiment, by providing a simulation of the transmission trend under the control plan, can provide a decision basis for the government departments concerned by developing different control plans to determine the transmission trend under each control plan separately.

The technical solution according to an embodiment of the present invention, obtaining respective target track data corresponding to the assessment objects within the preset area in a plurality of time slices of the target time period, the preset area comprising a plurality of subareas, wherein the target track data is historical and/or predicted track data; determining a matching subarea to which each assessment object matches in each time slice based on the target track data, the matching subarea being one of the plurality of subareas; taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period; assessing the transmission trend by using the track data of the assessment objects, considering the contact process among different assessment objects, the technical effect of fine-grained assessment of the trend of infection of respective areas is achieved compared to analyzing the progress of regional disease and assessing the change trend for the population size within the area by a mathematical model (which may be classified as ordinary differential equation, partial differential equation, and network dynamics model).

Embodiment III

FIG. 3 is a schematic structural diagram of an assessment device for infectious disease transmission provided in Embodiment III of the present invention, which may be applicable to a scenario for assessing the transmission trend of infectious disease, which device may be implemented in software and/or hardware and may be integrated in a computer equipment.

As shown in FIG. 3, the assessment device of infectious disease transmission provided in this embodiment may comprise a track data acquisition module 310, an area matching module 320, an assessment module 330 and a moment switching module 340, wherein:

the track data acquisition module 310, which is configured for obtaining respective target track data corresponding to the assessment objects within the preset area in a plurality of time slices of the target time period, the preset area comprising a plurality of subareas, wherein the target track data is historical and/or predicted track data; the area matching module 320 is configured for determining a matching subarea to which each assessment object matches in each time slice based on the target track data, the matching subarea being one of the plurality of subareas; the assessment module 330 is configured for taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; the moment switch module 340 is configured for taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

Optionally, the track data acquisition module 310 is further configured for obtaining the respective non-segmented raw track data corresponding to the assessment objects within the preset area during the target time period; and, segmenting the respective non-segmented raw track data corresponding to the assessment objects within the preset area according to a plurality of time slices of the target time period to obtain the respective target track data corresponding to the assessment objects within the preset area in the plurality of time slices of the target time period.

Optionally, the infectious disease model is a SEIR model, the assessment module 330 is specifically configured for determining the infected subjects, carriers, recovered persons and uninfected subjects within the target subarea in the first time slice; simulating the infectious disease transmission among the infected subjects, carriers, recovered persons and uninfected subjects within the target subarea based on a SEIR model to obtain the transmission trend of the infectious disease within the target subarea in the first time slice.

Optionally, the track data acquisition module 310 is further particularly configured for receiving an initial assessment instruction generated by the user upon selecting at least the initial infection parameters, the preset area, and the target time period; obtaining respective target track data corresponding to the assessment objects within the preset area in a plurality of time slices of the target time period and the initial health status of the initial time slice based on the initial assessment instruction. The assessment module 330 is particularly configured for assessing the transmission of the disease among the assessment objects within the target subarea in the first time slice based on the infectious disease model and the respective initial health status corresponding to the assessment objects within the target subarea.

Optionally, the target track data is predicted track data, and the track data acquisition module 310 comprises: a target historical time determination unit configured for determining a historical time period corresponding to the target time period; determining a respective target historical time for which the plurality of time slices matches; a target history track data acquisition unit configured for querying from a historical track database, the track data of the target history corresponding to the target historical times that each assessment object within the preset area matches in each time slice, wherein the historical track database stores the historical track data of different users during the historical time period; and a predicted track data determination unit configured for taking the track data of the target history as the predicted track data to obtain the respective target track data corresponding to the assessment subjects within the preset area in a plurality of time slices of the target time period.

Optionally, the track data acquisition module 310 is specifically adapted to invoke a prepared control plan, the control plan being used to influence the travel of the assessment subjects and/or to influence the infectious disease transmission, and determining, based on the control plan, the respective target track data corresponding to the assessment objects within the preset area in a plurality of time slices of the target time period.

Optionally, the control plan comprises at least one of area lockdown, teleworking, and setting detection points, and the device is further adapted to replace, if the control plan comprises area lockdown, the predicted track data corresponding to a predicted subject affected by the area lockdown with another unaffected historical track data before the transmission simulation; if the control plan comprises teleworking, the predicted track data corresponding to a predicted subject affected by the teleworking at the affected time is replaced with the corresponding home location before the transmission simulation; and if the control plan comprises setting detection points, the detection probability is set at a corresponding target subarea, and the target track data corresponding to the predicted subject for which an abnormality is detected is replaced to a safe subarea among the plurality of subareas during the transmission simulation from the current time slice until the end of the target time period.

The assessment device for infectious disease transmission provided in the embodiments of the present invention may perform the assessment method for infectious disease transmission provided in any of the embodiments of the present invention, having functional modules and advantageous effects corresponding to the method. What is not exhaustively described in this embodiment of the present invention can be referred to the description in any method embodiments of the present invention.

Embodiment IV

Figure 4:
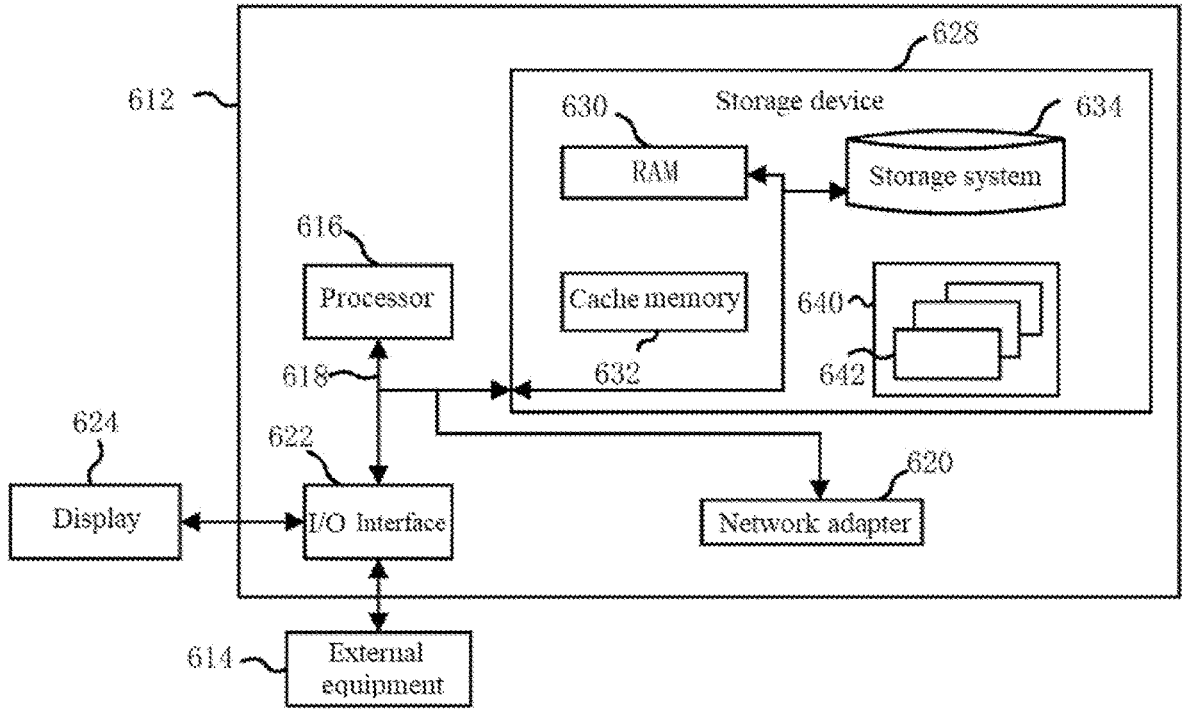
FIG. 4 is a schematic structural diagram of a computer equipment provided in Embodiment IV of the present invention.

FIG. 4 is the schematic structural diagram of a computer equipment provided in Embodiment IV of the present invention. FIG. 4 illustrates a block diagram of an exemplary computer equipment 612 suitable for implementing an embodiment of the present invention. The computer equipment 612 shown in FIG. 4 is merely an example and should not be construed as limiting the functionality and scope of use of embodiments of the present invention.

As shown in FIG. 4, the computer equipment 612 is represented in the form of a general-purpose computer equipment. Components of the computer equipment 612 may comprise, but are not limited to, one or more processors 616, a storage device 628, and a bus 618 connecting different system components comprising the storage device 628 and the processors 616.

Bus 618 represents one or more of several types of bus architectures, comprising a storage device bus or storage device controller, a peripheral bus, a graphics acceleration port, a processor, or a local bus using any of a variety of bus architectures. Examples of these architectures comprise, but are not limited to, the Industry Subversive Alliance (ISA) bus, the Micro Channel Architecture (MAC) bus, the Enhanced ISA bus, the Video Electronics Standards Association (VESA) local bus, and the Peripheral Component Interconnect (PCI) bus.

The computer equipment 612 typically comprises a variety of computer system readable medium. Such medium can be any available medium that can be accessed by the computer equipment 612, comprising volatile and nonvolatile medium, removable and non-removable medium.

The storage device 628 may comprise computer system readable medium in the form of volatile memory such as Random Access Memory (RAM) 630 and/or cache memory 632. The terminal 612 may further comprise other removable/non-removable, volatile/nonvolatile computer system storage medium. By way of example Only, storage system 634 may be provided for reading from and writing to a non-removable, nonvolatile magnetic medium (not shown in FIG. 4 and commonly referred to as "hard drive"). Although not shown in FIG. 4, a magnetic disk drive for reading from and writing to a removable, nonvolatile magnetic disk such as a "floppy disk" and a compact disk drive for reading from and writing to a removable, nonvolatile compact disk such as a Compact Disk Read-Only Memory (CD-ROM), Digital Video Disk-Read Only Memory (DVD-ROM) or other optical medium may be provided. In such cases, each drive may be connected to bus 618 through one or more data medium interfaces. The storage device 628 may comprise at least one computer program product having a set of (e.g., at least one) computer program modules configured to perform the functions of the various embodiments of the present invention.

The computer program/utility 640 having a set of (at least one) computer program modules 642, that may be stored in, for example, storage device 628, such computer program modules 642 comprise, but are not limited to, an operating system, one or more application computer programs, other computer program modules, and computer program data, and each of these examples or some combination may comprise an implementation of a network environment. The computer program modules 642 typically perform the functions and/or methods in the described embodiments of the present invention.

The computer equipment 612 may also communicate with one or more external equipment 614 (e.g., a keyboard, a pointing terminal, a display 624, etc.), may also communicate with one or more terminals that enable the assessment object to interact with the computing equipment 612, and/or with any terminal (e.g., network card, modem, etc.) that enables the computer equipment 612 to communicate with one or more other computing terminals. Such communication may be via Input/Output (I/O) Interface 622. Further, the computer equipment 612 may also communicate with one or more networks (e.g., Local Area Network (LAN), Wide Area Network (WAN), and/or public networks, such as the Internet) via the network adapter 620. As shown in FIG. 4, the network adapter 620 communicates with other modules of the computer equipment 612 via the bus 618. It should be appreciated that, although not shown in the figure, other hardware and/or software modules may be used in conjunction with the computer equipment 612, comprising but not limited to: microcode, terminal drives, redundant processors, external disk drive arrays, Redundant Arrays of Independent Disks (RAID) systems, tape drives, and data backup storage systems, etc.

The processor 616 performs various functional applications and data processing by running a computer program stored in the storage device 628, such as implementing a method of assessing the infectious disease transmission provided in any embodiment of the present invention, which method may comprise:

obtaining respective target track data corresponding to the assessment objects within the preset area in a plurality of time slices of the target time period, the preset area comprising a plurality of subareas, wherein the target track data is historical track data and/or predicted track data;

determining a matching subarea to which each assessment object matches in each time slice based on the target track data, the matching subarea being one of the plurality of subareas;

taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice;

taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

The technical solution according to an embodiment of the present invention, obtaining respective target track data corresponding to the assessment objects within the preset area in a plurality of time slices of the target time period, the preset area comprising a plurality of subareas, wherein the target track data is historical and/or predicted track data; determining a matching subarea to which each assessment object matches in each time slice based on the target track data, the matching subarea being one of the plurality of subareas; taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period; assessing the transmission trend by using the track data of the assessment objects, considering the contact process among different assessment objects, the technical effect of fine-grained assessment of the trend of infection of respective areas is achieved compared to analyzing the progress of regional disease and assessing the change trend for the population size within the area by a mathematical model (which may be classified as ordinary differential equation, partial differential equation, and network dynamics model).

Embodiment V

Embodiment V of the present invention also provides a computer readable storage medium having a computer program stored thereon, the computer program implements, when executed by a processor, an assessment method for the infectious disease transmissions as provided in any embodiment of the present invention, the method may comprise:

obtaining respective target track data corresponding to the assessment objects within the preset area in a plurality of time slices of the target time period, wherein the preset area comprises a plurality of subareas, and the target track data are historical track data and/or predicted track data;

determining a matching subarea to which each assessment object matches in each time slice based on the target track data, the matching subarea being one of the plurality of subareas;

taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice;

taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period.

The computer-readable storage medium of embodiments of the present invention may employ any combination of one or more computer-readable medium. The computer-readable medium may be a computer-readable signal medium or a computer-readable storage medium. The computer readable storage medium may be, for example—but not limited to—an electrical, magnetic, optical, electromagnetic, infrared, or semiconductor system, apparatus, or device, or any combination of the above. More specific examples of computer-readable storage medium (a non-exhaustive list) comprise: electrical connection having one or more wires, portable computer disk, hard disk, Random Access Memory (RAM), Read-Only Memory (ROM), Erasable Programmable Read-Only Memory (EPROM or flash memory), optical fiber, portable Compact Disk Read-Only Memory (CD-ROM), optical storage device, magnetic storage device, or any suitable combination of the above. In the context of this document, a computer-readable storage medium may be any tangible medium that contains or stores a computer program that can be used by or in combination with an instruction execution system, apparatus, or device.

The computer-readable signal medium may comprise a data signal propagated in a baseband or as part of a carrier wave that carries computer-readable program code. Such propagated data signals may take a variety of forms, comprising, but not limited to, electromagnetic signals, optical signals, or any suitable combination thereof. The computer-readable signal medium may also be any computer-readable medium other than a computer-readable storage medium that sends, propagates, or transmits a program for use by or in conjunction with an instruction execution system, apparatus, or device.

The computer program code contained on the storage medium may be transmitted using any appropriate medium, comprising but not limited to wireless, wireline, optical fiber cable, RF, etc., or any suitable combination of the foregoing.

Computer program code for performing the operations of the present invention may be written in one or more computer programming languages or combinations thereof, the computer programming languages comprising object-oriented computer programming languages—such as Java, Smalltalk, C++, and also comprising conventional procedural computer programming languages, such as the "C" programming language or similar computer programming languages. The computer program code may be executed entirely on the assessment object computer, partially on the assessment object computer, as a stand-alone software package, partially on the assessment object computer and partially on a remote computer, or entirely on a remote computer or terminal. In the case involving a remote computer, the remote computer may be connected to the assessment object computer via any kind of network—comprising a Local Area Network (LAN) or a Wide Area Network (WAN)—or, alternatively, may be connected to an external computer (e.g., using an Internet Service Provider to connect via the Internet connection).

The technical solution according to an embodiment of the present invention, obtaining respective target track data corresponding to the assessment objects within the preset area in a plurality of time slices of the target time period, the preset area comprising a plurality of subareas, wherein the target track data is historical and/or predicted track data; determining a matching subarea to which each assessment object matches in each time slice based on the target track data, the matching subarea being one of the plurality of subareas; taking the initial time slice as a first time slice, taking at least one of the plurality of subareas as a target subarea in the first time slice, assessing the assessment subjects within the target subarea based on the infectious disease model and the preset initial infection parameters to determine a transmission trend of the infectious disease among the assessment subjects within the preset area in the first time slice; taking the next time slice as the first time slice, re-performing the step of taking at least one of the plurality of subareas as a target subarea in the first time slice, assessing the assessment objects within the target subarea based on the infectious disease model and the preset initial infection parameters until the end of the target time period to determine a transmission trend of the infectious disease among the assessment objects within the preset area during the target time period; assessing the transmission trend by using the track data of the assessment objects, considering the contact process among different assessment objects, the technical effect of fine-grained assessment of the trend of infection of respective areas is achieved compared to analyzing the progress of regional disease and assessing the change trend for the population size within the area by a mathematical model (which may be classified as ordinary differential equation, partial differential equation, and network dynamics model).

Note that the above are only the preferred embodiments of the present invention and the applied technical principles. Those skilled in the art will appreciate that the present invention is not limited to the particular embodiments described herein, and that various obvious changes, readjustments and substitutions will now be apparent to those skilled in the art without departing from the scope of the invention. Therefore, although the present invention has been described in some detail by the above embodiments, the present invention is not limited to the above embodiments, and may comprise other equivalent embodiments without departing from the spirit of the invention, and the scope of which is determined by the scope of the appended claims.

What is claimed is:

1. An assessment method for infectious disease transmission, comprising:
    actively acquiring, by a computer system and for each of a plurality of time slices of a target time period, respective target track data corresponding to assessment objects within a preset area and associating the acquired target track data with corresponding subareas of the preset area, wherein
    the preset area comprises a plurality of subareas,
    the actively acquiring includes sampling only the subarea having a number of persons that is greater than or equal to a preset threshold, and
    the target track data are historical track data and/or predicted track data;
    processing, by the computer system, the acquired target track data to determine a matching subarea to which each assessment object matches in each time slice based on the target track data, the matching subarea being one of the plurality of subareas;
    executing, by the computer system, an infectious disease model to assess, for an initial time slice as a first time slice and at least one of the plurality of subareas taken as a target subarea in the first time slice, the assessment subjects within the target subarea based on preset initial infection parameters to determine a transmission trend of an infectious disease among the assessment subjects within the preset area in the first time slice;
    updating, by the computer system and based on the determined transmission trend for the preceding time slice, at least one of the infection parameters and the target track data for the corresponding assessment objects,
    wherein the updating comprises updating, for each subarea, one or more infection-state categories of the assessment objects, including infected subjects, carriers, recovered persons, or uninfected subjects, based on the determined transmission trend for the preceding time slice;
    executing, by the computer system, the infectious disease model to assess, for a next time slice as a second time slice and another one of the plurality of subareas taken as the target subarea in the second time slice, the assessment objects within the target subarea based on the updated infection parameters to determine the transmission trend of the infectious disease among the assessment subjects within the preset area in the second time slice, wherein the updating of the infection parameters and the target track data and the executing of the infectious disease model are performed until the end of the target time period to determine the transmission trend of the infectious disease among the assessment objects within the preset area during the target time period; and
    outputting, by the computer system to a user, the transmission trend determined for the target time period.

2. The method according to claim 1, wherein prior to the acquiring of the respective target track data corresponding to the assessment objects within the preset area in the plurality of time slices of the target time period, the method comprises:
    acquiring respective non-segmented raw track data corresponding to the assessment objects within the preset area during the target time period; and
    segmenting the respective non-segmented raw track data corresponding to the assessment objects within the preset area according to the plurality of time slices of the target time period to obtain the respective target track data corresponding to the assessment objects within the preset area in the plurality of time slices of the target time period.

3. The computer system, comprising:
    one or more processors; and
    a storage device for storing one or more computer programs, wherein
    the one or more computer programs, when executed by the one or more processors, enable the one or more processors to implement the assessment method for infectious disease transmission according to claim 2.

4. A non-transitory computer-readable storage medium, on which a computer program is stored, wherein the computer program, when executed by a processor, implements the assessment method for infectious disease transmission according to claim 2.

5. The method according to claim 1, wherein the infectious disease model is a SEIR model, and the assessing of the assessment subjects within the target subarea based on the preset initial infection parameters, comprises:
    determining the infected subjects, carriers, recovered persons and uninfected subjects within the target subarea in the first time slice; and
    simulating the infectious disease transmission among the infected subjects, carriers, recovered persons and uninfected subjects within the target subarea based on the SEIR model to obtain the transmission trend of the infectious disease within the target subarea in the first time slice.

6. The computer system, comprising:
    one or more processors; and
    a storage device for storing one or more computer programs, wherein;
    the one or more computer programs, when executed by the one or more processors, enable the one or more processors to implement the assessment method for infectious disease transmission according to claim 5.

7. A non-transitory computer-readable storage medium, on which a computer program is stored, wherein the computer program, when executed by a processor, implements the assessment method for infectious disease transmission according to claim 5.

8. The method according to claim 1, wherein the actively acquiring of the respective target track data corresponding to the assessment objects within the preset area in the plurality of time slices of the target time period comprises:

receiving an initial assessment instruction generated by the user upon selecting at least the initial infection parameters, the preset area, and the target time period;

acquiring the respective target track data corresponding to the assessment objects within the preset area in the plurality of time slices of the target time period and an initial health status at the initial time slice based on the initial assessment instruction;

wherein the assessing of the assessment subjects within the target subarea based on the preset initial infection parameters comprises:

assessing the infectious disease transmission among the assessment objects within the target subarea in the first time slice based on respective initial health status corresponding to the assessment objects within the target subarea.

9. The computer system, comprising:

one or more processors; and a storage device for storing one or more computer programs, wherein the one or more computer programs, when executed by the one or more processors, enable the one or more processors to implement the assessment method for infectious disease transmission according to claim 8.

10. A non-transitory computer-readable storage medium, on which a computer program is stored, wherein the computer program, when executed by a processor, implements the assessment method for infectious disease transmission according to claim 8.

11. The method according to claim 1, wherein the target track data is predicted track data, and the actively acquiring of the respective target track data corresponding to the assessment objects within the preset area in the plurality of time slices of the target time period comprises:

determining a historical time period corresponding to the target time period;

determining a respective target historical time for which the plurality of time slices matches;

querying from a historical track database, track data of target history corresponding to the target historical times that each assessment object within the preset area matches in each time slice, wherein the historical track database stores the historical track data of different users during the historical time period; and taking the track data of the target history as the predicted track data to obtain the respective target track data corresponding to the assessment subjects within the preset area in the plurality of time slices of the target time period.

12. The computer system, comprising:

one or more processors; and a storage device for storing one or more computer programs, wherein the one or more computer programs, when executed by the one or more processors, enable the one or more processors to implement the assessment method for infectious disease transmission according to claim 11.

13. A non-transitory computer-readable storage medium, on which a computer program is stored, wherein the computer program, when executed by a processor, implements the assessment method for infectious disease transmission according to claim 11.

14. The method according to claim 1, wherein the target track data is predicted track data, and the actively acquiring of the respective target track data corresponding to the assessment objects within the preset area in the plurality of time slices of the target time period comprises:

invoking a prepared control plan, the control plan being used to influence travel of the assessment subjects and/or to influence the infectious disease transmission, and determining, based on the control plan, the respective target track data corresponding to the assessment objects within the preset area in the plurality of time slices of the target time period.

15. The computer system, comprising:

one or more processors; and a storage device for storing one or more computer programs, wherein the one or more computer programs, when executed by the one or more processors, enable the one or more processors to implement the assessment method for infectious disease transmission according to claim 14.

16. A non-transitory computer-readable storage medium, on which a computer program is stored, wherein the computer program, when executed by a processor, implements the assessment method for infectious disease transmission according to claim 14.

17. The method according to claim 14, wherein the control plan comprises at least one of area lockdown, teleworking, and setting detection points, the method further comprising:

if the control plan comprises area lockdown, replacing the predicted track data corresponding to a predicted subject affected by the area lockdown with another unaffected historical track data before transmission simulation;

if the control plan comprises teleworking, replacing the predicted track data corresponding to a predicted subject affected by the teleworking at the time slice with corresponding home location before transmission simulation; and if the control plan comprises setting detection points, setting a detection probability at a corresponding target subarea, and replacing the target track data corresponding to the predicted subject for which an abnormality is detected with a safe subarea among the plurality of subareas during transmission simulation from current time slice until the end of the target time period.

18. The computer system comprising:

one or more processors; and a storage device for storing one or more computer programs, wherein the one or more computer programs, when executed by the one or more processors, enable the one or more processors to implement the assessment method for infectious disease transmission according to claim 1.

19. A non-transitory computer-readable storage medium, on which a computer program is stored, wherein the computer program, when executed by a processor, implements the assessment method for infectious disease transmission according to claim 1.

20. An assessment device for infectious disease transmission, comprising:

a processor programmed to:

actively acquire, for each of a plurality of time slices of a target time period, respective target track data corresponding to assessment objects within a preset area and associate the acquired target track data with corresponding subareas of the preset area, wherein the preset area comprising a plurality of subareas, the acquired target track data includes only a sampled subarea having a number of persons that is greater than or equal to a preset threshold, and the target track data are historical and/or predicted track data;

process the acquired target track data to determine a matching subarea to which each assessment object matches in each time slice based on the target track data, the matching subarea being one of the plurality of subareas;

execute an infectious disease model to assess, for an initial time slice as a first time slice and at least one of the plurality of subareas taken as a target subarea in the first time slice, the assessment subjects within the target subarea based on preset initial infection parameters to determine a transmission trend of an infectious disease among the assessment subjects within the preset area in the first time slice;

update, based on the determined transmission trend for the preceding time slice, at least one of the infection parameters and the target track data for the corresponding assessment objects, wherein, for each subarea, one or more infection-state categories of the assessment objects is updated, including infected subjects, carriers, recovered persons, or uninfected subjects, based on the determined transmission trend for the preceding time slice;

execute the infectious disease model to assess, for a next time slice as a second time slice and another one of the plurality of subareas taken as the target subarea in the second time slice, the assessment objects within the target subarea based on the updated infection parameters to determine the transmission trend of the infectious disease among the assessment subjects within the preset area in the second time slice, wherein the infection parameters and the target track data are updated and the infectious disease model is executed until the end of the target time period to determine the transmission trend of the infectious disease among the assessment objects within the preset area during the target time period; and output to a user the transmission trend determined for the target time period.

* * * * *